United States Patent
Curmi et al.

(10) Patent No.: US 8,932,553 B2
(45) Date of Patent: Jan. 13, 2015

(54) METHOD FOR MANUFACTURING CUBIC DIAMOND NANOCRYSTALS

(75) Inventors: Patrick Curmi, Evry (FR); Jean-Paul Boudou, Chatenay-Malabry Cedex (FR); Alain Thorel, Evry Cedex (FR); Fedor Jelezko, Stuttgart (DE); Mohamed Sennour, Evry Cedex (FR)

(73) Assignees: Institut National de la Sante et de la Recherche Medical (INSERM), Paris (FR); Armines, Paris (FR); Universitaet Stuttgart, Stuttgart (DE); Centre National de la Recherche Scientifique, Paris (FR)

( * ) Notice: Subject to any disclaimer, the term of this patent is extended or adjusted under 35 U.S.C. 154(b) by 317 days.

(21) Appl. No.: 13/255,691

(22) PCT Filed: Mar. 8, 2010

(86) PCT No.: PCT/EP2010/052910
§ 371 (c)(1), (2), (4) Date: Oct. 7, 2011

(87) PCT Pub. No.: WO2010/102977
PCT Pub. Date: Sep. 16, 2010

(65) Prior Publication Data
US 2012/0022231 A1    Jan. 26, 2012

(30) Foreign Application Priority Data
Mar. 9, 2009 (EP) .................................. 09305216

(51) Int. Cl.
*C01B 31/00* (2006.01)
*B01J 3/06* (2006.01)
(Continued)

(52) U.S. Cl.
CPC ............... *C01B 31/065* (2013.01); *C01B 31/14* (2013.01); *C01B 31/083* (2013.01); *B01J 2/00* (2013.01); *C01B 31/06* (2013.01); *B82Y 30/00* (2013.01); *B82Y 40/00* (2013.01); *Y10S 977/773* (2013.01)

USPC ........... 423/446; 423/445 R; 977/773; 546/32

(58) Field of Classification Search
None
See application file for complete search history.

(56) References Cited

U.S. PATENT DOCUMENTS

| 4,828,582 | A * | 5/1989 | Frushour .......................... 51/293 |
| 5,861,349 | A * | 1/1999 | Vereschagin et al. ........... 501/86 |
| 7,416,141 | B2 * | 8/2008 | Dobbs ............................. 241/21 |
| 2010/0068974 | A1 * | 3/2010 | Dumm et al. .................... 451/28 |

(Continued)

FOREIGN PATENT DOCUMENTS

EP     1 990 313      11/2008
WO   WO 2009/094750   8/2009

OTHER PUBLICATIONS

Boudou et al.; High Yield Fabrication of Fluorescent Nanodiamonds; Nanotechnology; 235602; May 2009.*

*Primary Examiner* — Guinever Gregorio
(74) *Attorney, Agent, or Firm* — Whitham Curtis Christofferson & Cook, PC

(57) ABSTRACT

A method for manufacturing cubic diamond nanocrystals (10) comprising the following successive steps: (a) providing crystalline diamond powder where the maximum particle size of the powder is equal or more than 2 um and equal or less than 1 mm; (b) milling said crystalline micron diamond powder using nitrogen jet milling micronization so as to manufacture a fine powder; (c) nanomilling the fine powder of step b) using a planetary tungsten carbide ball mill; (d) acid treating the nanomilled powder of step c); (e) extracting the cubic diamond nanocrystals (10) by centrifugation. Advantageously round-shaped cubic diamond nanocrystals are manufactured.

9 Claims, 3 Drawing Sheets

(51) Int. Cl.
*B01F 3/08* (2006.01)
*C01B 31/06* (2006.01)
*C01B 31/14* (2006.01)
*C01B 31/08* (2006.01)
*B01J 2/00* (2006.01)
*B82Y 30/00* (2011.01)
*B82Y 40/00* (2011.01)

(56) References Cited

U.S. PATENT DOCUMENTS

| | | | |
|---|---|---|---|
| 2010/0272627 A1* | 10/2010 | Sung | 423/446 |
| 2011/0020646 A1* | 1/2011 | West et al. | 428/401 |
| 2011/0151226 A1* | 6/2011 | Twitchen et al. | 428/220 |
| 2013/0083134 A1* | 4/2013 | Wu | 347/70 |

* cited by examiner

METHOD FOR MANUFACTURING CUBIC DIAMOND NANOCRYSTALS

CROSS-REFERENCE TO RELATED APPLICATIONS

This application is a 371 application of PCT/EP2010/052910 filed Mar. 8, 2010, and claims priority to European Application 09305216.5 filed Mar. 9, 2009.

The present invention relates to a method for manufacturing cubic diamond nanocrystals. The invention relates also to a cubic diamond nanocrystal that can be manufactured according to the method of the present invention.

Nanodiamonds are ultrasmall highly crystallized c-diamond. Nanodiamond size is usually equal or less than 100 nm and can be equal or less than about 10 nm, as for example about 5 nm.

Nanodiamonds have recently attracted a growing interest for applications in physics, chemistry and biology because of intrinsic fluorescence related to optically active defects.

According to different embodiments, they can be used as following:
- isolated diamond colors centers are of use in physics as single photon source for quantum computing, quantum cryptography, and NV (nitrogen vacancy) doped nanodiamonds can also be used as magnetic field sensors reaching atomic (sub-nm) spatial resolution and sensitivity in the order of mG for innovative nanoscale imaging magnetometry;
- in biology, the exceptional photostability of diamond's color centers opens up many applications in single molecule imaging and tracking. Indeed, less than 10 nm fluorescent nanodiamonds are ideally tailored for single-particle tracking for subcellular dynamics: such a small size reduces dramatically the impact on diffusion in cellular media and absence of blinking makes much easier trajectory reconstruction with less need for tracking algorithms to solve the frame-to-frame correspondence; they can also be used for quantitative aspects of biochemistry and of living processes (DNA-chip, quantitative PCR, immuno-detection of gene products in health and disease) since they sustain long term repetitive measurements which is not achievable with conventional fluorophores; in biology, the possibility to label molecules, (nucleic acids, peptides or proteins) with photoluminescent ultrasmall nanodiamonds opens novel prospects for quantitative biology;
- in material science and industry, pure and structurally well defined diamond nanoparticles can beneficially be used as seeding substrate for thin film CVD diamond synthesis and replace detonation nanodiamonds actually used for that aim. Diamond nanoparticles of controlled shape can be used as polishing material where ultralow roughness surfaces are needed such as in the hard disk computer industry. They can also be used for the fabrication of cutting material or for specific applications such as bioelectronics or for the next generation of integrated circuits. Nanodiamond can advantageously be used to coat lens and materials to obtain hard unalterable overlays.

Commonly used nanodiamonds are detonation nanodiamond where the diamond material originates from a detonation. Diamond particles with a diameter of circa 5 nm are formed when detonating a mixture of RDX (cyclotrimethylene-trinitramine) and TNT (trinitrotoluene).

After the synthesis, diamond is extracted from the soot using high-temperature high-pressure boiling in acid for a long period. The detonation nanodiamond grains mostly have diamond cubic lattice, are structurally imperfect and their shape is not uniform but comprises a plurality of facets.

The major barriers to the practical use of known nanodiamonds, such as detonation nanodiamonds, are the poor reliability of production methods and the non uniform shape of said nanodiamonds.

Thus the goal of the present invention is to provide a method for manufacturing cubic diamond nanocrystals that is reliable and suitable to manufacture uniform shaped nanocrystals.

This object is obtained according to the invention by a method for manufacturing cubic diamond nanocrystals comprising the following successive steps:
(a) providing crystalline diamond powder where the maximum particle size of the powder is equal or more than 2 µm and equal or less than 1 mm;
(b) milling said crystalline micron diamond powder using nitrogen jet milling micronization so as to manufacture a fine powder where the maximum particle size of the said fine powder is less than 2 µm;
(c) nanomilling the fine powder of step b) using a planetary tungsten carbide ball mill so as to manufacture a nanomilled powder comprising particles which maximum size is equal or less to 100 nm;
(d) acid treating the nanomilled powder of step c) so as to dissolve possible tungsten carbide particles that may have been produced in step c);
(e) extracting the cubic diamond nanocrystals by centrifugation.

Thanks to the method of the invention, nanocarbon material made of ultrasmall round-shape cubic diamond nanocrystals with typical size below 10 nm has been obtained.

The method of the present invention opens avenues for the industrial cost-effective production of pure or doped ultrasmall highly crystallized C-diamond nanoparticles for numerous applications such as in physics, material industry, chemistry, biology.

According to different embodiments of the present invention that may be combined:
- the particles of the crystalline micron diamond powder of step (a) have a maximum size comprised between 10 µm and 200 µm;
- the nitrogen jet milling micronization of step (c) last from 1 to 5 hours with a grinding pressure of at least 5 bars;
- the nanomilling of step (c) is implemented with WC+6% Co alloy bowl, lid and balls with ball size comprised between 5 to 30 mm;
- the nanomilling of step (c) is implemented with a plurality of successive periods separated by cooling periods so as the outside bowl wall temperature remains less than about 60° C. as for example equal or less than about 50° C.;
- the acid treating of step (d) comprises an autoclave treating with hydrofluoric and nitric acid mixture at a temperature comprised between 100° C. and 200° C.;
- during the extraction of step (e) ultra pure water is added to the sample resulting from the acid treating of step (d), said mixture is centrifuged and a first acid pellet is collected after discarding the acid supernatant;
- the first acid pellet is suspended in a small volume of ultra pure water, up to a pH equal or less than 1, said mixture is centrifuged and a second pellet is collected after discarding out the acid supernatant;

the second pellet is suspended in ultra pure water, neutralized with aqueous ammonia solution and centrifuged, and where the resulting supernatant is pooled and desalted by filtration.

The invention also relates to a cubic diamond nanocrystal which maximum size is equal or less to 100 nm wherein:
the diamond nanocrystal is round-shaped;
the diamond nanocrystal's surface comprises amorphous carbon layer where the number of atomic range of said layer is equal or less to 1;
the diamond nanocrystal consists of carbon comprising:
0 to 2000 ppm dopant (s)
less or equal to 50 ppm impurity(ies).

According to different embodiments, the cubic diamond nanocrystal may have following features that may be combined:
said nanocrystal is fluorescent and the dopant(s) is (are) nitrogen (N) or nitrogen combined with nickel (Ni);
said nanocrystal is not fluorescent and the dopant(s) is (are) chosen in the list consisting of boron (B), phosphorus (P);
the maximum size of the diamond nanocrystal is equal or less to 100 nm, can be equal or less than 10 nm, as for example about 5 nm.

The invention is also directed to a molecule labelled with any of preceding cubic diamond nanocrystal.

The invention also relates to a method of labelling a molecule comprising grafting a preceding cubic diamond nanocrystal.

The invention also relates to the use of preceding cubic nanocrystals in the use of the cubic diamond nanocrystal in the technical fields chosen in the list consisting of biomolecule labelling, biomolecule vectorisation, bioanalysis, quantum information processing, magnetometry, imaging techniques, chemical vapour deposition diamond synthesis, nanocomposite components.

The invention is further described in the detailed description of non limiting examples and embodiments as depicted and explained below.

In the drawings:
FIGS. 1 to 4 show transmission electron microscopy images and data of cubic diamond nanocrystals according to the present invention;
FIG. 5 shows a lognormal distribution of cubic diamond nanocrystals obtained according to the method of the present invention;
FIG. 6 shows an atomic force microscopy plot of a cubic diamond nanocrystal according to the present invention;
FIGS. 7a and b show spectroscopy plots of a cubic diamond nanocrystal according to the present invention.

According to an embodiment of the method of the present invention, cubic diamond nanocrystals are obtained as following:
the raw initial material is a highly crystalline synthetic micron diamond powder (commercialized as "Element Six PDA999 80-100") containing 80-100 mesh (187-150 μm) blocky, very uniformly cubo-octahedral shaped diamond crystals with extremely high toughness, thermal stability and impact strength;
to convert these microdiamonds into smaller particles, nitrogen jet milling autogeneous micronization is used and is preferred to planetary milling with stainless steel beads which causes severe contamination by iron compounds;
a sample of 250 g of the raw initial material is first micronized into a fine pure powder for 2 h in a 100 AFG fluidised bed opposed jet mill (commercialized by the company Hosokawa-Alpine, Germany) with a nitrogen flow rate of 60 m$^3$/h and a high grinding pressure (8 bars). After this step, a fine pure gray powder (with 97% of particles having sizes below 2 μm) is obtained;
the nanomilling procedure is then started, to convert the jet milling product into nanodiamonds (ND), using a ten grams aliquot from this gray micronized powder. The aliquot is ball milled under argon using a planetary ball mill named "Vario Planetary Mill, Pulverisette 4" (commercialized by the company Fritsch, Germany) with hard alloy WC+6% Co bowls and lids equipped with two valves (for milling under argon) and thirty 10 mm balls made with the same WC-Co cemented carbide. The powder-to-ball weight ratio R is 1/35. The absolute speed of the main disk is 400 rpm and the relative rotation speed of the vials with respect to the supporting disk is −2.17;
the program extends for 72 h as follows: the aliquot is ball milled for successive periods of 15 min, each separated by a 30 min cooling period (24 h effective grinding time). The temperature measured on the outside bowl wall is about 50° C. This programmed stepwise grinding mode is found more convenient than flowing liquid nitrogen around the vial to control the milling temperature between room temperature and 50° C.;
after milling, the beads are recovered by sieving and the powder sample is named milled diamond (MD). The finest tungsten carbide particles produced by milling present in the MD sample, and not recovered by sieving, are dissolved by harsh acid treatment: a 750 mg aliquot of the MD sample is placed in a 100 ml Teflon autoclave (200 ml "Zeoclave"—commercialized by the company Autoclave France) with 30 ml of hydrofluoric and nitric acid mixture (2/1 v/v) at 150° C. 48 h;
after completion of the acid treatment, an excess of "Milli-Q" ultrapure water (MQW), up to 100 ml, is added to the sample which is then mechanically dispersed before centrifugation (4000×g, 30 min at 25° C.) since the diamond sample precipitates in these acid conditions, the collected pellet is firm enough to pour out and discard the acid supernatant. To refine ND purification, this first pellet is suspended by strong shaking in a small volume of MQW. After centrifugation (4000×g, 30 min) the strongly acid supernatant is discarded and the pellet which contained precipitated nanodiamonds is then suspended in 50 ml of MQW. This new suspension is finally neutralized with aqueous ammonia solution and centrifuged again (4000×g, 30 min). The resulting supernatant containing fine diamond nanoparticles is stored for further processing. The residual pellet is resuspended (in 50 ml of MQW) and centrifuged (4000×g, 30 min) twice more times to complete the extraction of the fine diamond nanoparticles. The three neutral supernatants are then pooled and desalted by tangential flow filtration using a Millipore Pellicon XL cassette equipped with a Biomax membrane. The purified samples obtained here are named P (residual pellet) and ND (pooled, concentrated and desalted supernatants). The three types of samples are dried using a Mold Rotavapor. An aliquot is taken for X-ray diffraction and surface group analysis. Another one is resuspended in MQW for transmission electron microscopy observations and EDX analysis. The P and ND masses are expressed either relative to the MD mass or the total mass of the dried pure diamond (P+ND).

Preparation yield according to this embodiment is following, in weight % of the nanomilled powder of step c):
ND=10.6%
P=59.9%
Contamination (WC and others)=29.5%.

Transmission electron microscopy analyses are performed on a "FEI F-20ST" (commercialized by the company Philips) field emission gun transmission microscope equipped with super-twin polar pieces and operated at 200 kV. Energy dispersive X-ray (EDX) analysis coupled with TEM is used to identify the elemental composition of selected areas. Images are recorded at approximately Scherzer defocus on a CCD multiscan camera after astigmatism corrections, and eventually filtered via the Digital Micrograph software. Materials for transmission electron microscopy, prepared by ultrasonic dispersion of the samples in water for 5 mm, are deposited on a copper grid coated with holey carbon. The deposited suspensions are thereafter dried in air prior to transmission electron microscopy analyses. To avoid any electron irradiation damage, that could induce allotropic transformations of carbon materials, a reduced beam intensity is used and no phase change is observed, even after long exposure, as currently observed for detonation nanodiamond. X-ray diffraction (XRD) is used to determine the sample structure and composition before and just after milling. The data are collected using a X-ray diffractometer "XRD-6000", commercialized by the company Shimadzu Lab, with a radiation Cu (K$\alpha\lambda$) =1.54056 Å.

Analysis of the surface groups is done by temperature-programmed desorption mass-spectrometry. A small dried sample of about 5 mg of diamond nanocrystals is placed in a crucible and heated from 100 to 1450° C. at 30° C. min$^{-1}$ at atmospheric pressure in helium with one volume percent of neon (99/1, vol/vol) at a flow rate of 10 cm$^3$ min$^{-1}$. Product gases are continuously monitored and quantified with a mass spectrometer. The CO evolution profile is corrected from the m/z 28 contribution due to molecular nitrogen. The system is calibrated using gas mixtures in pure He with 1% Ne. The signal amplitude of each mass is compared to the m/z 20 signal amplitude of Ne. Physically desorbing water from heated samples produces a broad peak, probably due to interactions between polar water molecules and the inner walls of the transfer line between oven and detector. The integrated water peak is used to assess sample moisture content, and hence to correct gas yields with respect to organic carbon or total carbon content on a dry, ash-free basis.

The fully purified ND sample, obtained after decontamination and fine extraction, is made of pure nanocrystalline diamonds as shown on FIGS. 1 to 4.

FIG. 1 shows ND cubic diamond nanocrystals where the scale bar is 20 nm.

FIG. 2 shows a more detailed view of a ND diamond nanocrystal. The distance between the {111} parallel lattice planes is equal to a sin $\theta \approx 2.06$ Å, where a=3.5625 Å is the unit cell dimension and $\theta=0.6154$ rad is the angle between the {111} and the {110} planes. The distance between {400} parallel lattice planes is 0.25 a≈0.89 Å.

HRTEM fast Fourier transform (FFT) phase images corresponding to the (110) lattice fringes did not show any local distortion of the diamond lattice. Since the nanodiamonds are randomly deposited on the observation support (holey carbon coated TEM copper grid), the shadows of the polyhedrons, formed by the diamond Bragg planes on the support, appear as deformed flat polygons with an ellipsoidal envelop and an aspect ratio varying from 1.13 to 1.75 (mean value=1.37 for the 2 to 50 nm particle size range). Indeed, the unsharp polygonal shadows (as shown on FIG. 3) most probably result from the projection of euhedral diamond not perfectly aligned on the planar support.

Interestingly, the rounded shape of these particles, which derives from the initial uniformly cubo-octahedral shaped diamond crystals, is noticeably different from the angular shape of commercial diamond nanoparticles obtained by steel ball milling of Ib type HPHT inclusion-rich micron diamond crystals selected for their friability.

Diffraction data of a ND crystal are reported on FIG. 4.

To study the distribution of the ND crystals, the diameters d corresponding to the minor axis of the ellipse are taken instead of the diameter of a sphere of equivalent cross-sectional area on the image: $d=2(A/p)^{1/2}$, where A is the projected area of the nanoparticle. The distribution of the ND crystals shows excess skewness and kurtosis so that they can be better fitted with the equation for the standard lognormal ND crystals distribution with a mode occurring at 3.25 and a mean value of 3.5±0.3 as shown on FIG. 5. The lognormal character of the distribution probably results from the fact that, for a given magnification and set of instrument parameters, there is a resolution limit below which no size information is detectable. The mean sizes (3.25 & 3.5 nm) of the ND crystals is much below the minimum size (30 nm) predicted for diamond grit particles produced by fracture, and is of the same order of magnitude as those reported for the smallest synthetic or natural nanodiamonds. Said sizes of the ND crystals of the invention are close to their predicted physico-chemical stability limit.

Cubic diamond nanocrystals obtained according to the preceding manufacturing embodiment have been studied in view of their potential fluorescence characteristics. Nanocrystals which size is comprised between 200 to 400 µm have been electron irradiated and annealed so as to create nitrogen vacancies (NV).

Optical observation of said doped diamond nanocrystals using bright field transmission microscopes shows violet compounds. Optical observation of said doped diamond nanocrystals using fluorescence microscopy shows red compounds.

In the photoluminescence spectrum, the fluorescence intensity I is plotted according to the wavelength.

Said spectrum is a typical NC center emission photoluminescence spectrum with an intensity maximum at about 725 nm.

Figure 1:
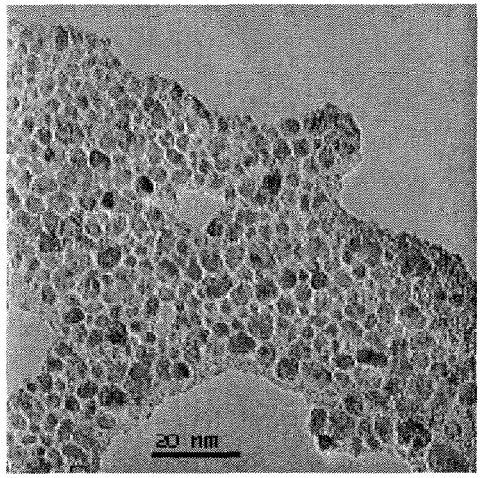
Figure 2:
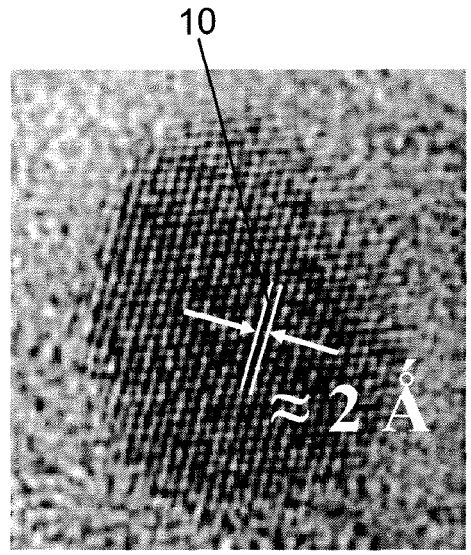
Figure 3:
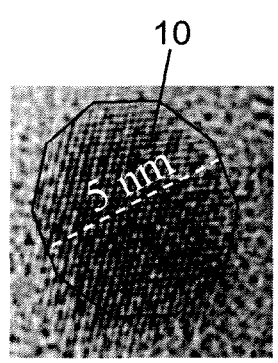
Figure 4:
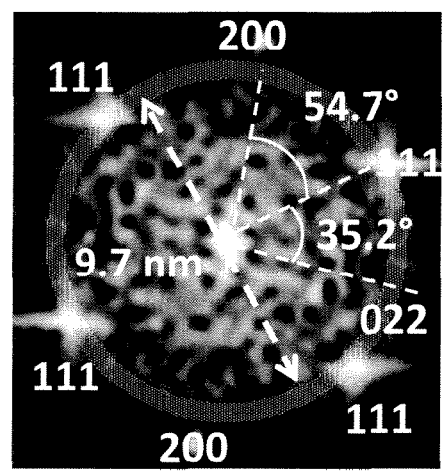
Figure 5:
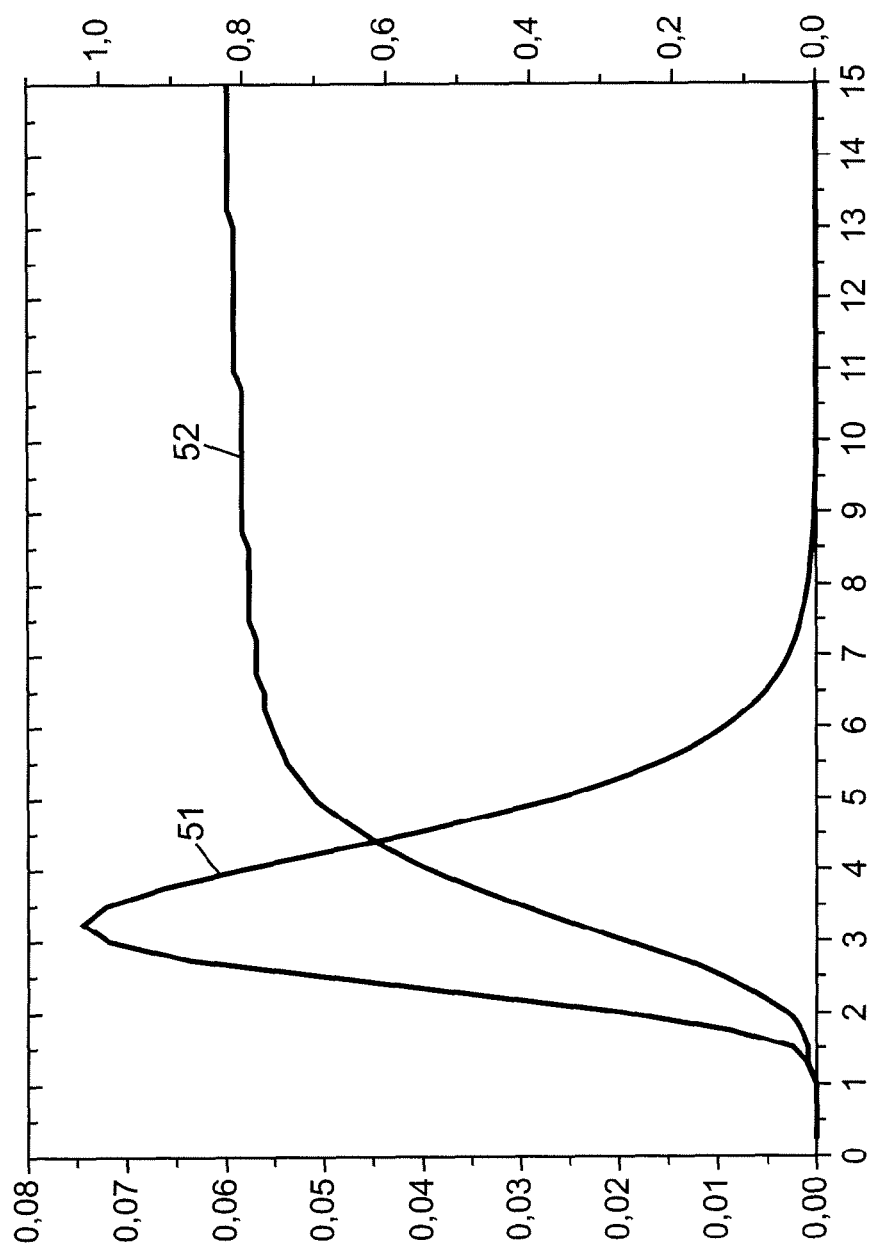
Figure 6:
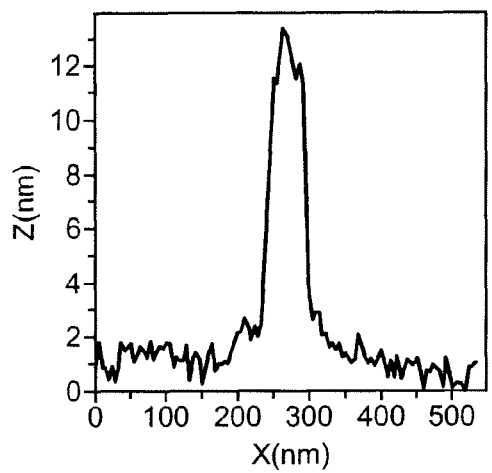
FIG. 6 shows an atomic force microscopy (AFM) plot of such a doped diamond nanocrystal where the size of the crystal can be estimated around 250 to 300 nm.
Figure 7A:
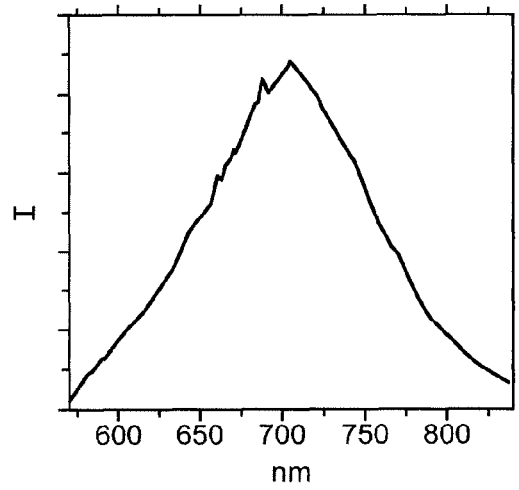
FIG. 7a shows a photoluminescence spectrum of the doped diamond nanocrystal which AFM plot is reported on FIG. 6.
Figure 7B:
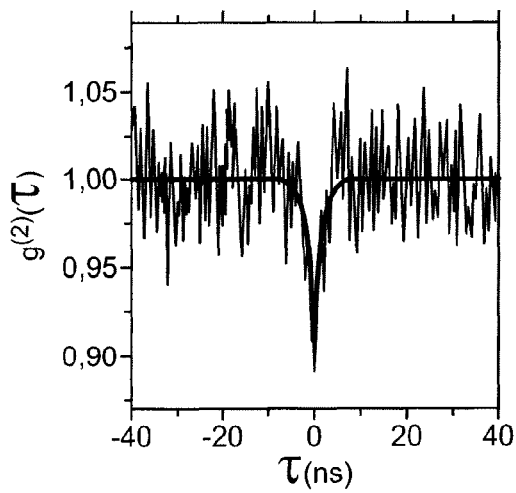

FIG. 7b shows a second-order fluorescence autocorrelation function $g^{(2)}(\tau)$ for the same diamond nanocrystal. Analysis of contrast of dip of said function allows determining the number of fluorescing defects. In the present example, the contrast is 0.08 and corresponds to 12 NV emitters in the diamond nanocrystal.

It has thus been demonstrated that the method according to the present invention makes possible to manufacture new and advantageous cubic diamond nanocrystals.

The invention has been described above with the aid of embodiments without limitation of the general inventive concept; in particular the parameters of the method for manufacturing cubic diamond nanocrystals of the invention may be varied and are not limited to the examples discussed.

The invention claimed is:

1. A method for manufacturing cubic diamond nanocrystals comprising the following successive steps:

(a) providing crystalline diamond powder where the maximum particle size of the diamond powder is equal or more than 2 μm and equal or less than 1 mm and where the particles of the diamond powder have a cubo-octahedral shape;

(b) milling said crystalline micron diamond powder using nitrogen jet milling micronization so as to manufacture a fine powder where the maximum particle size of the said fine powder is less than 2 μm;

(c) nanomilling the fine powder of step b) using a planetary tungsten carbide ball mill so as to manufacture a nanomilled powder comprising particles which maximum size is equal or less to 100 nm;

(d) acid treating the nanomilled powder of step c) so as to dissolve possible tungsten carbide particles that may have been produced in step c);

(e) extracting the cubic diamond nanocrystals by centrifugation, wherein the cubic diamond nanocrystals have a rounded shape.

2. The method of claim 1 wherein the particles of the crystalline micron diamond powder of step (a) have a maximum size comprised between 10 μm and 200 μm.

3. The method of claim 1 wherein the nitrogen jet milling micronization of step (b) lasts from 1 to 5 hours with a grinding pressure of at least 5 bars.

4. The method of claim 1 wherein the nanomilling of step (c) is implemented with WC+6% Co alloy bowl, lid and balls with ball size comprised between 5 to 30 mm.

5. The method of claim 1 wherein the nanomilling of step (c) is implemented with a plurality of successive periods separated by cooling periods so as the outside bowl wall temperature remains less than about 60° C.

6. The method of claim 1 wherein the acid treating of step (d) comprises an autoclave treating with hydrofluoric and nitric acid mixture at a temperature comprised between 100° C. and 200° C.

7. The method of claim 1 wherein during the extraction of step (e) ultra pure water is added to the sample resulting from the acid treating of step (d), said mixture is centrifuged and a first pellet is collected after discarding the acid supernatant.

8. The method of claim 7 wherein the first pellet is suspended in ultra pure water with addition of sulphuric acid, up to a pH equal or less than 1, said mixture is centrifuged and a second pellet is collected after discarding out the acid supernatant.

9. The method of claim 8 wherein the second pellet is suspended in ultra pure water, neutralized with aqueous ammonia solution and centrifuged, and where the resulting supernatant is pooled and desalted by filtration.

* * * * *